US005795566A

United States Patent [19]
Joulain et al.

[11] Patent Number: 5,795,566
[45] Date of Patent: *Aug. 18, 1998

[54] DEODORANT COMPOSITIONS CONTAINING AT LEAST TWO ALDEHYDES AND THE DEODORANT PRODUCTS CONTAINING THEM

[75] Inventors: Daniel Joulain; Philippe Racine, both of Grasse, France

[73] Assignee: Robertet S.A., Grasse, France

[*] Notice: The term of this patent shall not extend beyond the expiration date of Pat. No. 4,840,792.

[21] Appl. No.: 357,995

[22] Filed: Dec. 16, 1994

Related U.S. Application Data

[63] Continuation of Ser. No. 908,810, Jul. 7, 1992, abandoned, which is a continuation of Ser. No. 640,388, filed as PCT/FR90/00371, May 28, 1990, abandoned.

[30] Foreign Application Priority Data

May 29, 1989 [FR] France .................................. 89 07279

[51] Int. Cl.$^6$ ........................................................ A61L 9/01
[52] U.S. Cl. .................... 424/76.1; 424/76.2; 424/76.3; 424/76.4; 424/76.5; 424/405; 424/45; 424/489; 424/76.8; 514/937; 514/944; 514/951
[58] Field of Search ........................ 424/76.1, 76.2, 424/76.5, 45, 405, 489, 76.3, 76.4, 76.8; 514/937, 944, 951

[56] References Cited

U.S. PATENT DOCUMENTS

| 2,875,131 | 2/1959 | Carpenter et al. | 424/76.1 |
| 3,509,254 | 4/1970 | Krotinger et al. | 424/76.1 |
| 4,229,410 | 10/1980 | Kosti | 424/76.1 |
| 4,840,792 | 6/1989 | Joulain et al. | 424/76.1 |

FOREIGN PATENT DOCUMENTS

| 0132038 | 1/1985 | European Pat. Off. . |
| 132038 | 1/1985 | European Pat. Off. . |
| 0247946 | 12/1987 | European Pat. Off. . |
| 1590898 | 5/1970 | France . |
| 2599042 | 11/1987 | France . |

OTHER PUBLICATIONS

CA95(17):144580y.

*Primary Examiner*—Raj Bawa
*Attorney, Agent, or Firm*—Browdy and Neimark

[57] ABSTRACT

Deodorant compositions containing at least two aldehydes include at least one aldehyde selected from acyclic aliphatic aldehydes, non-terpenic aliphatic aldehydes, non-terpenic alicyclic aldehydes, terpenic aldehydes, aliphatic aldehydes substituted by an aromatic group and bifunctional aldehydes; and one aldehyde selected from aldehydes possessing a non-aromatic unsaturation carried by the carbon which is alpha to the aldehyde, aldehydes possessing an unsaturation alpha to the aldehyde function conjugated with an aromatic ring, and the aldehydes in which the aldehyde group is on an aromatic ring.

31 Claims, No Drawings

DEODORANT COMPOSITIONS CONTAINING AT LEAST TWO ALDEHYDES AND THE DEODORANT PRODUCTS CONTAINING THEM

This application is a continuation of application Ser. No. 07/908,810, filed Jul. 7, 1992, abandoned, itself a continuation of application Ser. No. 07/640,388, filed as PCT/FR90/00371, May 28, 1990, abandoned.

FIELD OF THE INVENTION

The present invention relates to deodorant compositions containing at least two aldehydes and the deodorant products containing them.

BACKGROUND OF THE INVENTION

The search to combat bad odours has led to the use of numerous substances of great variety, for example phenol substances, essential oils, resins, aldehydes or ketones, alcohol derivatives, esters or others substances.

Compositions are always being sought which are more effective, for deodorizing and which optionally have an agreeable odour.

SUMMARY OF THE INVENTION

Notably various aldehydes have been used, mixed with numerous other products. After long studies, the Applicant has discovered that compositions containing an aldehyde chosen from one class, hereafter called class A, and an aldehyde chosen from another class, hereafter called class B, have remarkable deodorant properties, clearly superior to those of each of these compounds taken individually.

The subject of the present Application is deodorant compositions characterized in that they contain a first aldehyde chosen from the acyclic and non-terpenic aliphatic aldehydes, the non-terpenic alicyclic aldehydes, the terpenic aldehydes, the aliphatic aldehydes substituted by an aromatic group and the the bifunctional aldehydes (class A) and a second aldehyde chosen from the aldehydes possessing a non-aromatic unsaturation carried by the carbon in alpha position of the aldehyde function, the aldehydes possessing an unsaturation in alpha position of the aldehyde function conjugated with an aromatic ring and the aldehydes of which the function is carried by an aromatic ring (class B).

The acyclic and non-terpenic aliphatic aldehydes are preferably:
decanal,
undecanal,
dodecanal,
undecene-10-al,
2-methyl-undecanal,
2,6,10-trimethyl-9-undecene-al ("ADOXAL") and
2,3,5,5-tetramethyl-hexanal.

The non-terpenic alicyclic aldehydes are preferably:
1-formyl-2,4-dimethyl-2-cyclohexene and 1-formyl-3,5-dimethyl-4-cyclohexene (TRIPLAL®),
1-formyl-2,3,5-trimethyl-4-cyclohexene and 1-formyl-2,4,6-trimethyl-3-cyclohexene ("ISOCYCLOCITRAL"),
([5.2.1.0$^{0.6}$]-tricyclo-8-decylidene)-4-butanal (DUPICAL®),
2,6,10-trimethyl-9-undecene-al (ADOXAL®),
(4-methyl-3-pentene-yl)-4-cyclohexene-3-yl carboxaldehyde,
7-formyl-5-isopropyl-2-methyl-2,2,2-bicyclo-2-octene (MACEAL®), and
2-formyl-8-dimethyl-1,2,3,4,5,6,7,8-octahydro-naphthalene ("ALDEHYDE 111")>

The terpenic aldehydes are preferably:
citronellal 3,7-dimethyl-6-octen-1-al and
campholenic aldehyde.

The aliphatic aldehydes substituted by an aromatic group are preferably:
helional® α-methyl-3,4-methylene-dioxyhydrocinnamic aldehyde,
cyclamen aldehyde,
lilial,
canthoxal$^R$,
phenylacetic aldehyde,
3-phenyl-propionic aldehyde,
hydratropic aldehyde, By "bifunctional aldehyde" is meant aldehydes possessing moreover another function such as the ether-oxide or alcohol functions, preferably:
alkoxy-acetaldehydes,
w-hydroxy aldehydes (hydroxycitronellal, LYRALR, . . . ),
w-alkoxy-aldehydes.

The above aldehydes form class A.

Among the aldehydes of class B, the aldehydes which possess a non-aromatic type unsaturation carried by the carbon in the alpha position of the aldehyde function are preferably:
citral (neral and geranial),
myrtenal,
perilla aldehyde,
variously substituted 2-furyl carboxaldehydes.

The aldehydes which possess an ethylene unsaturation in alpha position, itself conjugated with an aromatic ring are preferably:
cinnamic aldehyde,
alpha-amylcinnamic aldehyde ("JASMONAL") or 2-pentyl-3-penyl-2-propenal,
alpha-hexylcinnamic aldehyde.

The aldehydes carried by an aromatic ring, moreover variously substituted, are preferably:
benzaldehyde,
anisic aldehyde,
heliotropine,
veratric aldehyde,
vanillin,
isovanillin, and
ethylvanillin.

The deodorant compositions according to the present invention contain an aldehyde from each of the above classes and can obviously contain three or more aldehydes as long as each of the two above classes are represented.

In the preferred conditions for implementing the invention described above, the first aldehyde is chosen preferably from the acyclic and non-terpenic aliphatic aldehydes, the alicyclic and non-terpenic aldehydes, the terpenic aldehydes, and the aliphatic aldehydes substituted by an aromatic group, the second aldehyde is preferably chosen from the aldehydes which possess a non-aromatic type unsaturation carried by the alpha carbon.

Quite particularly, the first aldehyde is chosen from the acyclic and non-terpenic aliphatic aldehydes and the second from those designated above.

Particularly interesting aldehyde pairs are notably the following pairs:

dodecanal and myrtenal, dodecanal and citral, adoxal and Perilla aldehyde, triplal and citral, maceal and citral, adoxal and myrtenal, decanal and citral, undecene-10-al and myrtenal, as well as the product pairs cited in the examples.

The aldehydes of classes A and B can be in relative proportions one to the other and preferably in proportions from 80/20 to 20/80, notably in proportions of 50/50.

The deodorant compositions above, in addition to their remarkable deodorant properties possess, moreover, fragrant properties themselves capable of replacing bad odours by their own smell.

The preferred compositions contain in addition a masking agent.

Therefore these compositions can be composed of at least one fragrant agent of agreeable smell such as those usually used in the perfume industry such as alcohols, essential oils, phenol substances, esters.

These deodorant compositions find their use in all conditions where the combating of bad smells, whatever their origin, is sought.

In addition the compositions described above can contain specific products, for example, bactericides.

These deodorant compositions are advantageously formulated according to standard techniques.

Another, subject of the present Application is deodorant products characterized in that they contain the compositions described above.

These products can be presented in the form of aerosol sprays, impregnated solid supports, liquids, creams, powders etc. They can be made according to methods known to one skilled in the art.

EXPERIMENTAL PART

The following examples illustrate the present invention, without however limiting it.

The effect on bad smells of the compositions according to the present invention were evaluated using the following devices:

Nitrogen is fed using a Y-shaped connector through two flow meters provided with a valve allowing the flow in each branch of the device to be regulated. This gas supplies two identical glass crystallizers of a 25 liter volume containing respectively a bad smelling mixture and the same mixture having added to it the test products, intended to neutralize this bad smelling mixture, by two gas currents of the same flow rate.

Each of the two crystallizers is provided with a removable glass lid and is also linked to a scent receptacle by a glass connection piece. A stop-plug allows either the passage of gas from the crystallizer to the scent receptacle or the isolation of this latter.

The scent receptacles are also provided with a glass lid.

Before each evaluation of the test products, two identical samples of a standard bad odour are prepared which are placed in each of the crystallizers.

Then 2 g of test products are placed on cellulose wadding which is placed in one of the two crystallizers. These are then closed using their lids and covered with an opaque cloth so that the evaluators carry out a blind test. The test product is in a 10 mM solution. When a product is tested by itself, a 2 g solution of this product is placed on the wadding and for a mixture of two products, a 1 g solution of each of the two is placed on the wadding.

The flow rate of the supporting gas is regulated at 2 liters/min in each of the two branches of the device for a period of 3 minutes.

Then the plugs are closed so as to isolate the scent receptacles from the rest of the system. The evaluators then come and smell both of the two scent receptacles, either immediately at the end of 3 minutes, or 5 minutes later.

The evaluators are asked to judge the differences in intensity and tonality of the odours between the two scent receptacles.

The evaluators are people trained to detect the differences of tonality and intensity of the odours.

The tests were conducted with a panel of 20 people and their responses noted and coded as follows:

−: no difference between the two receptacles or the wrong answer when asked where the products under test were to be found, ±: difference in tonality between the two receptacles but the odours are perceived to be bad-smelling, +: appreciable reduction in the bad smell in the receptacle where the product(s) under test is(are) to be found, ++: complete disappearance of the bad smell in the receptacle where the product(s) under test is(are) to be found.

The aldehydes chosen from class A or B were tested individually. The following results were obtained:

TABLE 1

| Class A | Class B | Effect at <1 mn | Effect at 5 mn |
|---------|---------|-----------------|----------------|
|         | citral  | −               | −              |
| helional |        | −               | +              |
| dodecanal |       | +               | +              |
|         | jasmonal | −              | +              |
| citronellal |     | +               | +              |

Then the aldehyde pairs belonging to the same class were tested. The results obtained were as follows:

TABLE 2

|                 | Pair                  | Pair              |
|-----------------|-----------------------|-------------------|
| Class A         | dodecanal/helional    |                   |
| Class B         |                       | citral/jasmonal   |
| Effect at <1 mn.| −                     | −                 |
| Effect at 5 mn. | ++                    | +                 |

Finally the aldehyde pairs belonging to classes A and B were tested. The results obtained were as follows:

TABLE 3

|                  | Pair     | Pair     | Pair        |
|------------------|----------|----------|-------------|
| Class A          | helional | helional | citronellal |
| Class B          | citral   | jasmonal | jasmonal    |
| Effect at <1 mn. | +        | −        | −           |
| Effect at 5 mn.  | +        | ++       | ++          |

In conclusion, the clearest and strongest neutralizing effect, not only immediately but also after a time lapse of 5 minutes, is obtained when aldehyde pairs both belonging to the two classes A and B are used.

N.B.: Dodecanal was tested in a 2.5 mM solution not 10 mM as with the other products, so as not to saturate the enclosed space with its odour.

Preparation of a Standard Bad-Smelling Odour 1 g of a solution at 1.000 ppm of propylamine and 1 g of a solution at 100 ppm of 3-mercapto-3-methyl-1-butanol is poured onto a clean cellulose wadding plug.

1. An Air-Freshener Aerosol Spray

An aerosol corresponding to the following composition is made (by volume):

| | |
|---|---|
| citronellal | 1% |
| jasmonal | 1% |
| 99% ethanol | 3% |
| Freon 11 | 57% |
| Freon 12 | 38% |

2. An Air-Freshener Aerosol Spray

An aerosol corresponding to the following composition is made (by volume):

| | |
|---|---|
| citral | 1.5% |
| jasmonal | 0.5% |
| 99% ethanol | 3.0% |
| Freon 11 | 57.0% |
| Freon 12 | 38.0% |

3. A liquid Deodorant and Disinfectant for Floors

A deodorant and disinfectant liquid corresponding to the following composition is made (by volume):

| | |
|---|---|
| ethoxylated nonylphenol with 10 moles of ethylene oxide | 7.0% |
| alkylmethylbenzylammonium chloride | 1.5% |
| citral | 0.5% |
| helional | 0.5% |
| de-ionized water | 90.5% |

4. A liquid Deodorant and Disinfectant for Floors a deodorant and disinfectant liquid corresponding to the following composition is made (by volume):

| | |
|---|---|
| ethoxylated nonylphenol with 10 moles of ethylene oxide | 7.0% |
| alkylmethylbenzylammonium chloride | 1.5% |
| dodecanal | 0.2% |
| helional | 0.8% |
| de-ionized water | 90.5% |

We claim:

1. Deodorant compositions consisting essentially of as active ingredients at least one first aldehyde and at least one second aldehyde, the ratio of said first aldehyde to said second aldehyde being from about 20:80 to about 80:20;

wherein said first aldehyde is selected from the group consisting of decanal; undecanal; dodecanal; 2,6,10-trimethyl-9-undecene-al; undecene-10-al; 2-methyl-undecanal; 2,3,5,5-tetramethyl-hexanal; 1-formyl-2,4-dimethyl-2-cyclohexene; 2-formyl-3,5-dimethyl-4-cyclohexene; 1-formyl-2,3,5-trimethyl-4-cyclohexene; 1-formyl-2,4,6-trimethyl-3-cyclohexene; [(5.2.1.0.6)-tricyclo-8-decylidene]-4-butanal; 2,6,10-trimethyl-9-undecene-al; (4-methyl-3-pentene-yl)-4-cyclohexene-3-yl carboxaldehyde; 7-formyl-5-isopropyl-2-methyl-2,2,2-bicyclo-2-octene; 2-formyl-8-dimethyl-1,2,3,4,5,6,7,8-octahydronaphthalene; citronellal; campholenic aldehyde; α-methyl-3,4-methylene-dioxyhydrocinnamic aldehyde; cyclamen aldehyde; lilial; canthoxal; phenylacetic aldehyde; 3-phenyl-propionic aldehyde; hydroxycitronellal; and hydratropic aldehyde;

wherein said second aldehyde is selected from the group consisting of citral; jasmonal; myrtenal; perilla aldehyde; cinnamic aldehyde; alpha-amylcinnamic aldehyde; alpha-hexylcinnamic aldehyde; benzaldehyde; anisic aldehyde; heliotropine; veratric aldehyde; vanillin; isovanillin; and ethylvanillin.

2. A deodorant composition according to claim 1 wherein said first aldehyde is selected from the group consisting of citronellal and campholenic aldehyde, and said second aldehyde is selected from the group consisting of citral, neral, geranial, and perilla aldehyde.

3. A deodorant composition according to claim 1 wherein said first aldehyde is selected from the group consisting of decanal; undecanal; dodecanal; 2,6,10-trimethyl-9-undecene-al; undecene-10-al; 2-methyl-undecanal; 2,3,5,5-tetramethyl-hexanal; 1-formyl-2,4-dimethyl-2-cyclohexene; 2-formyl-3,5-dimethyl-4-cyclohexene; 1-formyl-2,3,5-trimethyl-4-cyclohexene; 1-formyl-2,4,6-trimethyl-3-cyclohexene; [(5.2.1.0.6)-tricyclo-8-decylidene]-4-butanal; 2,6,10-trimethyl-9-undecene-al; (4-methyl-3-pentene-yl)-4-cyclohexene-3-yl carboxaldehyde; 7-formyl-5-isopropyl-2-methyl-2,2,2-bicyclo-2-octene; 2-formyl-8-dimethyl-1,2,3,4,5,6,7,8-octahydronaphthalene; citronellal; campholenic aldehyde; helional; cyclamen aldehyde; lilial; canthoxal; phenylacetic aldehyde; 3-phenyl-propionic aldehyde; and hydratropic aldehyde;

and said second aldehyde is selected from the group consisting of citral, neral, geranial, and perilla aldehyde.

4. A deodorant composition according to claim 1 wherein said first aldehyde is α-methyl-3,4-methylene-dioxyhydrocinnamic aldehyde and said second aldehyde is citral.

5. A deodorant composition according to claim 1 wherein said first aldehyde is α-methyl-3,4-methylene-dioxyhydrocinnamic aldehyde and said second aldehyde is 2-pentyl-3-phenyl-2-propenal.

6. A deodorant composition according to claim 1 wherein said first aldehyde is 3,7-dimethyl-6-octen-1-al and said second aldehyde is 2-pentyl-3-phenyl-2-propenal.

7. A deodorant composition according to claim 1 wherein said first aldehyde is present in an amount of 50% by volume and said second aldehyde is present in an amount of 50% by volume.

8. Deodorant compositions consisting essentially of a carrier selected from the group consisting of solid supports, liquids, creams, and powders, and, as active ingredients, at least one first aldehyde, and at least one second aldehyde, the ratio of said first aldehyde to said second aldehyde being from about 20:80 to about 80:20;

wherein said first aldehyde is selected from the group consisting of decanal; undecanal; dodecanal; 2,6,10-trimethyl-9-undecene-al; undecene-10-al; 2-methyl-undecanal; 2,3,5,5-tetramethyl-hexanal; 1-formyl-2,4-dimethyl-2-cyclohexene; 2-formyl-3,5-dimethyl-4-cyclohexene; 1-formyl-2,3,5-trimethyl-4-cyclohexene; 1-formyl-2,4,6-trimethyl-3-cyclohexene; [(5.2.1.0.6)-tricyclo-8-decylidene]-4-butanal; 2,6,10-trimethyl-9-undecene-al; (4-methyl-3-pentene-yl)-4-cyclohexene-3-yl carboxaldehyde; 7-formyl-5-isopropyl-2-methyl-2,2,2-bicyclo-2-octene; 2-formyl-8-dimethyl-1,2,3,4,5,6,7,8-octahydronaphthalene; citronellal; campholenic aldehyde; α-methyl-3,4-methylene-dioxyhydrocinnamic aldehyde; cyclamen aldehyde; lilial; canthoxal; phenylacetic aldehyde; 3-phenyl-propionic aldehyde; hydroxycitronellal; and hydratropic aldehyde;

wherein said second aldehyde is selected from the group consisting of citral; myrtenal; perilla aldehyde; cinnamic aldehyde; alpha-amylcinnamic aldehyde; alpha-hexylcinnamic aldehyde; benzaldehyde; anisic aldehyde; heliotropine; veratric aldehyde; vanillin; isovanillin; and ethylvanillin.

9. A deodorant composition according to claim 8 wherein said first aldehyde is selected from the group consisting of citronellal and campholenic aldehyde, and said second aldehyde is selected from the group consisting of citral, neral, geranial, and perilla aldehyde.

10. A deodorant composition according to claim 8 wherein said first aldehyde is selected from the group consisting of decanal; undecanal; dodecanal; 2,6,10-trimethyl-9-undecene-al; undecene-10-al; 2-methyl-undecanal; 2,3,5,5-tetramethyl-hexanal; 1-formyl-2,4-dimethyl-2-cyclohexene; 2-formyl-3,5-dimethyl-4-cyclohexene; 1-formyl-2,3,5-trimethyl-4-cyclohexene; 1-formyl-2,4,6-trimethyl-3-cyclohexene; [(5.2.1.0.6)-tricyclo-8-decylidene]-4-butanal; 2,6,10-trimethyl-9-undecene-al; 4-methyl-3-pentene-yl)-4-cyclohexene-3-yl carboxaldehyde; 7-formyl-5-isopropyl-2-methyl-2,2,2-bicyclo-2-octene; 2-formyl-8-dimethyl-1,2,3,4,5,6,7,8-octahydronaphthalene; citronellal; campholenic aldehyde; helional; cyclamen aldehyde; lilial; canthoxal; phenylacetic aldehyde; 3-phenyl-propionic aldehyde; and hydratropic aldehyde;

and said second aldehyde is selected from the group consisting of citral, neral, geranial, and perilla aldehyde.

11. A deodorant composition according to claim 8 wherein said first aldehyde is α-methyl-3,4-methylene-dioxyhydrocinnamic aldehyde and said second aldehyde is citral.

12. A deodorant composition according to claim 8 wherein said first aldehyde is α-methyl-3,4-methylene-dioxyhydrocinnamic aldehyde and said second aldehyde is 2-pentyl-3-phenyl-2-propenal.

13. A deodorant composition according to claim 8 wherein said first aldehyde is 3,7-dimethyl-6-octen-1-al and said second aldehyde is 2-pentyl-3-phenyl-2-propenal.

14. A deodorant composition according to claim 8 wherein said first aldehyde is present in an amount of 50% by volume and said second aldehyde is present in an amount of 50% by volume.

15. Deodorant compositions consisting essentially of at least one fragrance, and, as active ingredients, at least one first aldehyde, and at least one second aldehyde, the ratio of said first aldehyde to said second aldehyde being from about 20:80 to about 80:20;

wherein said first aldehyde is selected from the group consisting of decanal; undecanal; dodecanal; 2,6,10-trimethyl-9-undecene-al; undecene-10-al; 2-methyl-undecanal; 2,3,5,5-tetramethyl-hexanal; 1-formyl-2,4-dimethyl-2-cyclohexene; 2-formyl-3,5-dimethyl-4-cyclohexene; 1-formyl-2,3,5-trimethyl-4-cyclohexene; 1-formyl-2,4,6-trimethyl-3-cyclohexene; [(5.2.1.0.6)-tricyclo-8-decylidene]-4-butanal; 2,6,10-trimethyl-9-undecene-al; (4-methyl-3-pentene-yl)-4-cyclohexene-3-yl carboxaldehyde; 7-formyl-5-isopropyl-2-methyl-2,2,2-bicyclo-2-octene 2-formyl-8-dimethyl-1,2,3,4,5,6,7,8-octahydronaphthalene; citronellal; campholenic aldehyde; α-methyl-3,4-methylene-dioxyhydrocinnamic aldehyde; cyclamen aldehyde; lilial; canthoxal; phenylacetic aldehyde; 3-phenyl-propionic aldehyde; hydroxycitronellal; and hydratropic aldehyde;

wherein said second aldehyde is selected from the group consisting of citral; myrtenal; perilla aldehyde; cinnamic aldehyde; alpha-amylcinnamic aldehyde; alpha-hexylcinnamic aldehyde; benzaldehyde; anisic aldehyde; heliotropine; veratric aldehyde; vanillin; isovanillin; and ethylvanillin.

16. A deodorant composition according to claim 15 wherein said first aldehyde is selected from the group consisting of citronellal and campholenic aldehyde, and said second aldehyde is selected from the group consisting of citral, neral, geranial, and perilla aldehyde.

17. A deodorant composition according to claim 15 wherein said first aldehyde is selected from the group consisting of decanal; undecanal; dodecanal; 2,6,10-trimethyl-9-undecene-al; undecene-10-al; 2-methyl-undecanal; 2,3,5,5-tetramethyl-hexanal; 1-formyl-2,4-dimethyl-2-cyclohexene; 2-formyl-3,5-dimethyl-4-cyclohexene; 1-formyl-2,3,5-trimethyl-4-cyclohexene; 1-formyl-2,4,6-trimethyl-3-cyclohexene; [(5.2.1.0.6)-tricyclo-8-decylidene]-4-butanal; 2,6,10-trimethyl-9-undecene-al; (4-methyl-3-pentene-yl)-4-cyclohexene-3-yl carboxaldehyde; 7-formyl-5-isopropyl-2-methyl-2,2,2-bicyclo-2-octene; 2-formyl-8-dimethyl-1,2,3,4,5,6,7,8-octahydronaphthalene; citronellal; campholenic aldehyde; helional; cyclamen aldehyde; lilial; canthoxal; phenylacetic aldehyde; 3-phenyl-propionic aldehyde; and hydratropic aldehyde;

and said second aldehyde is selected from the group consisting of citral, neral, geranial, and perilla aldehyde.

18. A deodorant composition according to claim 15 wherein said first aldehyde is α-methyl-3,4-methylene-dioxyhydrocinnamic aldehyde and said second aldehyde is citral.

19. A deodorant composition according to claim 15 wherein said first aldehyde is α-methyl-3,4-methylene-dioxyhydrocinnamic aldehyde and said second aldehyde is 2-pentyl-3-phenyl-2-propenal.

20. A deodorant composition according to claim 15 wherein said first aldehyde is 3,7-dimethyl-6-octen-1-al and said second aldehyde is 2-pentyl-3-phenyl-2-propenal.

21. A deodorant composition according to claim 15 wherein said first aldehyde is present in an amount of 50% by volume and said second aldehyde is present in an amount of 50% by volume.

22. A method for deodorizing an environment which is afflicted with an offensive odor comprising adding to the environment an effective amount of a deodorant composition according to claim 1 to neutralize the offensive odor.

23. A method for deodorizing an environment which is afflicted with an offensive odor comprising adding to the environment an effective amount of a deodorant composition according to claim 8 to neutralize the offensive odor.

24. A method for deodorizing an environment which is afflicted with an offensive odor comprising adding to the environment an effective amount of a deodorant composition according to claim 15 to neutralize the offensive odor.

25. A deodorant composition according to claim 1 wherein said first aldehyde is α-methyl-3,4-methylene-dioxyhydrocinnamic adehyde or citronellal and said second aldehyde is citral or jasmonal.

26. A deodorant composition according to claim 1 wherein said first aldehyde is selected from the group consisting of dodecanol, aldoxal, triplal, maceal, adoxal, decanal, and undecene-10-al, and said second aldehyde is selected from the group consisting of myrtenal, citral, and perilla aldehyde.

27. A deodorant composition according to claim 8 wherein said first aldehyde is selected from the group consisting of dodecanol, aldoxal, triplal, maceal, adoxal, decanal, and undecene-10-al, and said second aldehyde is selected from the group consisting of myrtenal, citral, and perilla aldehyde.

28. A deodorant composition according to claim 15 wherein said first aldehyde is selected from the group consisting of dodecanol, aldoxal, triplal, maceal, adoxal, decanal, and undecene-10-al, and said second aldehyde is selected from the group consisting of myrtenal, citral, and perilla aldehyde.

29. A deodorant composition according to claim 15 wherein said first aldehyde is α-methyl-3,4-methylenedioxyhydrocinnamic aldehyde or dodecanal and said second aldehyde is citral or jasmonal.

30. A deodorant composition according to claim 8 wherein said first aldehyde is α-methyl-3,4-methylenedioxyhydrocinnamic aldehyde or dodecanal and said second aldehyde is citral or jasmonal.

31. A deodorant composition according to claim 15 wherein said first aldehyde is α-methyl-3,4-methylenedioxyhydrocinnamic aldehyde or dodecanal and said second aldehyde is citral or jasmonal.

* * * * *